United States Patent [19]
Gyory

[11] Patent Number: 5,380,271
[45] Date of Patent: Jan. 10, 1995

[54] ELECTROTRANSPORT AGENT DELIVERY DEVICE AND METHOD

[75] Inventor: J. Richard Gyory, San Jose, Calif.

[73] Assignee: ALZA Corporation, Palo Alto, Calif.

[21] Appl. No.: 950,627

[22] Filed: Sep. 24, 1992

[51] Int. Cl.⁶ .............................................. A61N 1/30
[52] U.S. Cl. ...................................... 604/20; 607/149
[58] Field of Search ................ 604/20; 128/798, 802, 128/803; 607/149–153

[56] References Cited

U.S. PATENT DOCUMENTS

| | | | |
|---|---|---|---|
| 4,250,878 | 2/1981 | Jacobsen et al. | 128/207.21 |
| 4,383,529 | 5/1983 | Webster | 604/20 |
| 4,474,570 | 10/1984 | Ariura et al. | 604/20 |
| 4,557,723 | 12/1985 | Sibalis | 604/20 |
| 4,706,680 | 11/1987 | Keusch et al. | 128/640 |
| 4,708,716 | 11/1987 | Sibalis | 604/20 |
| 4,722,726 | 2/1988 | Sanderson et al. | 604/20 |
| 4,731,926 | 3/1988 | Sibalis | 604/20 |
| 4,745,857 | 5/1988 | Putnam et al. | 101/44 |
| 4,764,164 | 8/1988 | Sasaki | 604/20 |
| 4,779,531 | 10/1988 | Ueno et al. | 101/163 |
| 4,863,757 | 9/1989 | Durand | 427/47 |
| 4,883,457 | 11/1989 | Sibalis | 604/20 |
| 4,896,598 | 1/1990 | Leech, Jr. | 101/170 |
| 4,917,761 | 4/1990 | Keep | 156/668 |
| 4,919,648 | 4/1990 | Sibalis | 604/20 |
| 4,928,587 | 5/1990 | Glover | 101/42 |
| 4,960,614 | 10/1990 | Durand | 427/54.1 |
| 4,978,569 | 12/1990 | Keep | 428/209 |
| 4,985,293 | 1/1991 | Keep | 428/209 |
| 4,989,607 | 2/1991 | Keusch et al. | 128/640 |
| 5,006,108 | 4/1991 | LaPrade | 604/20 |
| 5,032,109 | 7/1991 | Sibalis | 604/20 |
| 5,047,007 | 9/1991 | McNichols et al. | 604/20 |
| 5,050,498 | 9/1991 | Smith | 101/127.1 |
| 5,066,360 | 11/1991 | Daley et al. | 156/660 |
| 5,100,695 | 3/1992 | Kawakami et al. | 427/96 |
| 5,158,537 | 10/1992 | Haak et al. | 604/20 |
| 5,162,043 | 11/1992 | Lew et al. | 604/20 |

FOREIGN PATENT DOCUMENTS

410009  5/1934  United Kingdom .
9009413  8/1990  WIPO .

OTHER PUBLICATIONS

A. V. Schwalbach and J. A. Schwalbach, "Screen Process and Printing," Van Nostrand Reinhold Co., 1970, pp. 99–105.

Primary Examiner—C. Fred Rosenbaum
Assistant Examiner—Michael Rafa
Attorney, Agent, or Firm—D. Byron Miller; Edward L. Mandell; Steven F. Stone

[57] ABSTRACT

An electrical circuit (21) for an electrotransport agent delivery device (10), and a method for making same, is provided. The circuit (21) generally includes a plurality of electrically conductive circuit traces (71–77) deposited on a substrate (42). One or more electrical circuit components (61–63), such as batteries, resistors, capacitors and/or transistors, is mounted on the substrate (42) and are electrically connected to the circuit traces (71–77), using an electrically conductive adhesive. The circuit traces (71–77) and the adhesive contain an electrically conductive filler which renders the traces and the adhesive electrically conductive. Preferably, the electrically conductive filler is a material which is relatively non-toxic, such as silver, carbon and/or graphite. The electrical circuit components (61–63) may be connected to the circuit traces (71–77) using automated component attachment procedures. The circuit (21) does not require hand soldering of electrical components (61–63), such as batteries, to the circuit traces (71–77) and does not require the use of solder coating or other similar procedures to suppress corrosion of circuit traces that might otherwise occur. A silk screening process or a pad printing process can be used to deposit the circuit traces (71–77) on the substrate (42). An electrotransport agent delivery device (10) having this circuit (21) is much less likely to inadvertently introduce potentially toxic ions into a patient's body.

18 Claims, 3 Drawing Sheets

ELECTROTRANSPORT AGENT DELIVERY DEVICE AND METHOD

BACKGROUND OF THE INVENTION

1. Technical Field

This invention relates to an electrotransport agent delivery device and method having a reduced tendency to deliver extraneous and potentially toxic metal ions into the body. More specifically, this invention relates to a device for electrotransport delivery of a drug into the body, which device utilizes an electrical circuit without soldered electrical connections.

2. Background Art

The present invention concerns apparati for transdermal delivery of a therapeutic agent by electrotransport. The therapeutic agent or species to be delivered may be partially or completely charged and be delivered by electromigration (charged particle flow induced by an imposed electrical field); the agent or species may be completely uncharged (i.e., zero percent ionized) and be delivered by electroosmosis (flow of uncharged particles induced by an imposed electrical field); or the agent or species may be partly charged and be delivered by electromigration, by electroosmosis, or by a combination of these two processes. Electroosmosis has also been referred to as electrohydrokinesis, electroconvection, and electrically-induced osmosis. In general, electroosmosis of a therapeutic species into a tissue results from the migration of solvent, in which the species is contained, as a result of the application of electromotive force to the therapeutic species reservoir.

As used herein, the term "electrotransport" refers broadly to each of the following iontophoretic phenomena: (1) the delivery of charged drugs or agents by electromigration and/or electroosmosis; (2) the delivery of uncharged drugs or agents by the process of electroosmosis; and/or (3) the delivery of a mixture of charged and uncharged drugs or agents by electromigration and/or electroosmosis.

As used herein, the terms "agent" and "drug" are used interchangeably and are intended to have broad application and to refer to any therapeutically active substance that is delivered to a living organism to produce a desired, usually beneficial, effect. In general, this includes therapeutic agents in all of the major therapeutic areas including, but not limited to: anti-infectives such as antibiotic and antiviral agents; analgesics, including fentanyl, sufemanil, buprenorphine and analgesic combinations; anesthetics, anorexics; antiarthritics; antiasthmatic agents, such as terbutaline; anticonvulsants; antidepressants; antidiabetic agents; antidiarrheals; antihistamines; anti-inflammatory agents; antimigraine preparations; antimotion sickness preparations, such as scopolamine and ondansetron; antinauseants; antineoplastics; antiparkinson drugs; cardiostimulants, such as dobutamine; antipruritics; antipsychotics; antipyretics; antispasmodics, including gastrointestinal and urinary; anticholinergics; sympathomimetrics; xanthine derivatives; cardiovascular preparations, including calcium blockers, such as nifedipine; beta blockers; beta-agonists, such as salbutamol and ritodrine; antiarrythmics; antihypertensives, such as atenolol; ACE inhibitors, such as enalapril; diuretics; vasodilators, including general, coronary, peripheral and cerebral; central nervous system stimulants; cough and cold preparations; decongestants; diagnostics; hormones, such as parathyroid hormone; hypnotics; immunosuppressives; muscle relaxants; parasympatholytics; parasympathomimetrics; prostaglandins; proteins; peptides; psychostimulants; sedatives and tranquilizers.

The invention is also useful in active delivery of peptides, polypeptides, proteins and other macromolecules. These macromolecular substances typically have a molecular weight of at least 300 Daltons, and more typically have a molecular weight in the range 300–40,000 Daltons. Specific examples of peptides and proteins in this weight range include, without limitation: LHRH; LHRH analogs, such as buserelin, gonadorelin, nafarelin and leuprolide; GHRH; GHRF; insulin; insulotropin; heparin; calcitonin; octreotide; endorphin; TRH; NT-36 (chemical name: N=[[(s)- 4-oxo-2-azetidinyl]-carbonyl]-L-histidyl-L-prolinamide), liprecin; pituitary hormones, such as HGH, HMG, HCG and desmopressin acetate; follicle luteoids; $\alpha$ANF; growth factors, such as growth factor releasing factor (GFRF), $\beta$MSH; somatostatin; bradykinin; somatotropin; platelet-derived growth factor; asparaginase; bleomycin sulfate; chymopapain; cholecystokinin; chorionic gonadotropin; corticotropin (ACTH); erythropoietin; epoprostenol (platelet aggregation inhibitor); glucagon; himlog; hyaluronidase; interferon;; intedeukin-1; intedeukin-2; menotropins (urofollitropin (FSH) and LH); oxytocin; streptokinase; tissue plasminogen activator; urokinase; vasopressin; desmopressin; ACTH analogs; ANP; ANP clearance inhibitors; angiotensin II antagonists; antidiuretic hormone agonists; antidiuretic hormone antagonists; bradykinin antagonists; CD4; ceredase; CSF's; enkephalins; FAB fragments; IgE peptide suppressors; IGF-1, neurotrophic factors; colony stimulating factors; parathyroid hormone and agonists; parathyroid hormone antagonists; prostaglandin antagonists;pentigetide; protein C; protein S; renin inhibitors; thymosin alpha-1; thrombolytics; TNF; vaccines; vasopressin antagonists analogs; alpha-1 anti-trypsin (recombinant); and TGF-beta.

Iontophoretic devices for delivering ionized drugs through the skin have been known since the early 1900's. Deutsch, in U.K. Patent No. 410,009 (1934), describes an iontophoretic device that overcame one of the disadvantages of such early devices, namely that the patient needed to be immobilized near the source of electric current. The Deutsch device was powered by a galvanic cell formed from the electrodes and the material containing the drug to be transdermally delivered. The galvanic cell produced the current necessary for iontophoretically delivering the drug. This device thus allowed the patient to move around during iontophoretic drug delivery, and thus imposed substantially less interference with the patient's daily activities.

In presently known electrotransport devices, at least two electrodes are used. Both of these electrodes are disposed so as to be in intimate electrical contact with some portion of the skin of the body. One electrode, called the active or "donor" electrode, is the electrode from which the substance, agent, medicament, drug precursor or drug is delivered into the body through the skin by electrotransport. The other electrode, called the "counter" or return electrode, serves to close the electrical circuit through the body. In conjunction with the patient's skin contacted by the electrodes, the circuit is completed by connection of the electrodes to a source of electrical energy, such as a battery. For example, if an ionic substance to be driven into the body is positively charged, then the positive electrode (the anode)

will be the active electrode and the negative electrode (the cathode) will serve to complete the circuit. If an ionic substance to be delivered is negatively charged, then the cathodic electrode will be the active electrode and the anodic electrode will be the counter electrode.

Furthermore, existing electrotransport devices have a reservoir or source of the beneficial agent or drug, preferably an ionized or ionizable species (or a precursor of such species) that is to be delivered or introduced into the body by electrotransport. Examples of such reservoirs or sources include: a pouch as described by Jacobsen in U.S. Pat. No. 4,250,878; a pre-formed gel body as disclosed in U.S. Pat. No. 4,382,529, issued to Webster; and a generally conical or domed molding disclosed in U.S. Pat. No. 4,722,726, issued to Sanderson et al. Such drug reservoirs are connected to the anode or the cathode of an electrotransport device to provide a fixed or renewable source of one or more desired species or agents.

Perhaps the most common use of electrotransport today is in diagnosing cystic fibrosis by delivering pilocarpine transdermally. Transdermal electrotransport delivery of pilocarpine stimulates sweat production, and the sweat is collected and is analyzed for its chloride ion content. Chloride ion concentration in excess of certain limits suggests the possible presence of the cystic fibrosis disease.

All electrotransport agent delivery devices utilize an electrical circuit to electrically connect the power source (e.g., a battery) to the electrodes. In very simple devices, such as those disclosed by Ariura et al. in U.S. Pat. No. 4,474,570, the "circuit" is merely an electrically conductive wire used to connect the battery to an electrode. Other devices use a variety of electrical components to control the amplitude, polarity, timing, waveform shape, etc. of the electric current supplied by the power source. See, for example, U.S. Pat. No. 5,047,007, issued to McNichols et al.

More recently, there has been an effort to develop miniaturized iontophoretic drug delivery devices which are adapted to be worn on the skin, unobtrusively and under a patient's clothing. The electrical components in such miniaturized iontophoretic drug delivery devices are also preferably miniaturized, and may be in the form of either integrated circuits (i.e., microchips) or small printed flexible circuits. Although printed circuits are desirable from a cost standpoint, there are potential problems with the use of conventional printed circuits when the circuits come into contact with the liquid solvent (usually water) used to solubilize the agents contained in the donor and counter electrode assemblies. For example, conventional printed circuits are formed by printing or otherwise depositing electrically conductive pathways on a flexible substrate, usually in the form of a polymer sheet. Electronic components, such as batteries, resistors, pulse generators, capacitors, etc., are then electrically connected, for example, by soldering to the printed or deposited electrically conductive pathways to form a complete circuit.

Presently, most flexible circuits are manufactured using a copper-coated polyimide or polyester sheet that is etched to remove the copper coating from preselected areas of the sheet. The copper-coated portions of the sheet remain after the etching process and define the desired circuit traces. Circuit components are usually soldered onto the circuit, using solder that contains lead, copper and other metals to promote good electrical contact.

This technology has certain associated problems when used in an electrotransport system. First, the circuits must undergo cleaning procedures, after etching and soldering, that may leave soluble (e.g., water soluble) chemical residues on the circuit that may be pharmaceutically undesirable or even toxic. Second, untreated copper circuit traces corrode over time, which limits the shelf life of the circuit and of any associated pharmaceutical electrotransport system. A common technique for suppressing the corrosion of copper circuit traces entails solder-coating the traces. Solder contains metals, such as lead, that are toxic and that can present a serious health hazard if delivered into the body. If the solder used in the electrical circuit inadvertently comes into contact with the liquid solvent contained in an electrode assembly (e.g., a drug solution in a donor electrode assembly, or an electrolyte salt solution in a counter electrode assembly) during operation of an associated electrotransport system, extraneous metal ions from the solder, such as copper and/or lead, can be inadvertently introduced into one or both of the electrode assemblies, and transported into the patient's body. This is particularly troublesome in electrotransport devices that are adapted to be worn and used over extended periods of time. Thus, there is a need for an electrotransport device that utilizes a flexible electrical circuit, which circuit has a lessened tendency to generate and introduce undesirable extraneous ions into the hydrated electrode assemblies. There is a further need for an electrotransport agent delivery device that utilizes a flexible electrical circuit, which circuit is substantially free of solder and other materials which can act as a source of undesirable extraneous ions.

DISCLOSURE OF THE INVENTION

These needs are met by an electrotransport device having an electrical circuit adapted to be electrically connected to a power source and an electrode assembly. The electrical circuit comprises a substrate (e.g., a polyester or polyimide film substrate) having one or more circuit traces of an electrically conductive ink. One or more electrical components (such as a battery, capacitor, resistor, transistor, etc.) is then electrically connected to the circuit traces, using an electrically conductive adhesive that provides an electrical connection between the circuit trace and the electrical component. Preferably, the electrically conductive ink and the electrically conductive adhesive are substantially free of potentially toxic materials, such as lead, nickel, cadmium, copper, chromium, tungsten and iron. Preferably, the conductive ink and conductive adhesive contain carbon, silver, gold, platinum, palladium, iridium, zinc and/or titanium and have resistivities of less than 1 Ohm-cm, most preferably less than 0.01 Ohm-cm.

MODES FOR CARRYING OUT THE INVENTION

Figure 1:
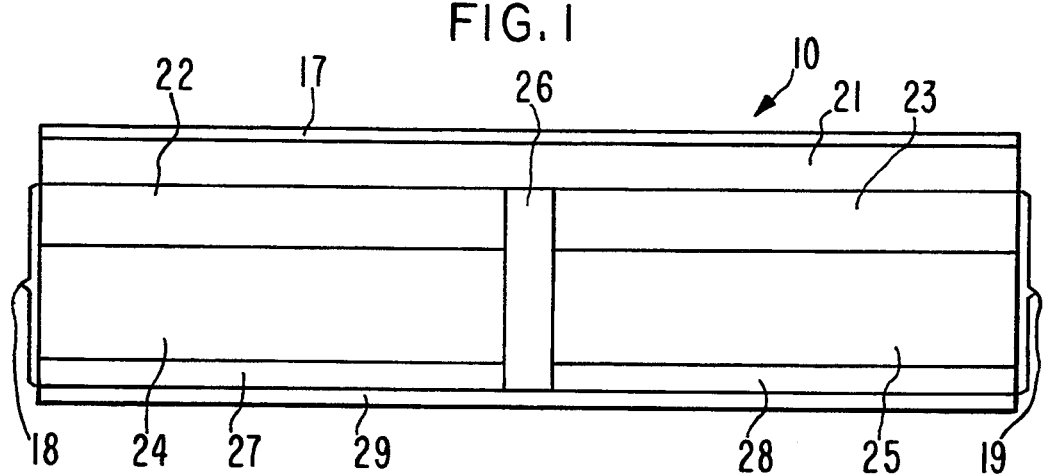
FIG. 1 is a sectional side view of an electrotransport delivery device constructed in accordance with the invention.

FIG. 1 is a sectional side view of an electrotransport device 10, for example, for transdermal delivery of a drug or other medical agent. It should be understood that the device 10 can have essentially any convenient size or shape, whether square, oval, circular, or tailored for a specific location on the skin. As illustrated, the device 10 would generally be applied to the skin of a patient by first removing a strippable release liner 29 (optional) and adhering the device to the skin by means of adhesive layers 27 and 28. The device 10 has a backing layer 17 that is preferably formed of a water-impermeable sheet material such as high density polyethylene. Positioned beneath the backing layer 17 is an electronic circuit 21 that contains one or more electrical components, such as a source of electrical power (e.g., one or more batteries arranged in series or in parallel) and, optionally, other electrical components for controlling the amplitude, polarity, timing, waveform shape and frequency of the electric current supplied by the power source. Examples of typical electrical components within a circuit 21 include resistors, transistors, current regulators, pulse generators, timing devices, on/off switches, etc. The circuit 21 generally contains all of the electrical components necessary to deliver electric current of predeterminable characteristics to the electrode assemblies 18 and 19. The circuit 21 is preferably flexible, and generally includes one or more electronic components mounted on a thin, flexible substrate (e.g., a polymer film), which electronic components are electrically connected by circuit traces deposited on the substrate in the form of a conductive ink. The circuit 21, and methods for its manufacture, will be described in detail below.

The device 10 further comprises electrode means or assemblies 18 and 19, separated from one another by an electrical insulator 26. The assemblies 18 and 19 and the insulator 26 form a single, self-contained unit. For purposes of illustration, the electrode assembly 18 is sometimes referred to as the donor electrode assembly, and electrode assembly 19 is sometimes referred to as the counter electrode assembly. These designations of the electrode assemblies are not critical, and may be reversed in any particular device or in operation of the device shown.

As shown in FIG. 1, the donor electrode assembly 18 includes a donor electrode 22 positioned adjacent to an agent-containing donor reservoir 24. The counter electrode assembly 19 includes a counter electrode 23 positioned adjacent to an agent-containing counter reservoir 25. The current-distributing electrodes 22 and 23 may be formed of a metal screen or foil, or a polymer matrix loaded with metal powder, powdered graphite, carbon fibers, or any other suitable electrically conductive material. The reservoirs 24 and 25 can be polymer matrices or gel matrices. Natural or synthetic polymer matrices may be employed. An insulator 26, preferably formed of an electrically insulating and ion-impermeable material, acts as a barrier between the electrode assemblies 18 and 19 to prevent short-circuiting of the device 10. The insulator 26 can be an air gap, an ion-impermeable and electrically insulating polymer or adhesive, or another suitable barrier to ion and electron flow.

As an alternative to the ion-conducting adhesive layers 27 and 28, the device 10 can be adhered to the skin by means of an adhesive overlay of the type conventionally used in some transdermal drug delivery devices. Generally speaking, an adhesive overlay contacts the skin around the perimeter of the device to maintain the reservoirs 24 and 25 in agent-transmitting relation with the patient's skin.

In a typical device 10, the donor reservoir 24 contains a supply of the drug or other beneficial agent to be delivered, and the counter reservoir 25 contains a suitable electrolyte such as, for example, sodium chloride, sodium phosphate, or mixtures thereof. Alternatively, the device 10 may contain one or more drugs or other beneficial agents in each reservoir 24 and 25; and in that manner, both electrode assemblies 18 and 19 would function as donor electrode assemblies (anode and cathode). For example, drug cations can be delivered through the skin from an anode electrode assembly, while drug anions can be delivered from a cathode electrode assembly. Alternatively, neutral drug molecules can be delivered by electrotransport from either or both of the anode and cathode electrode assemblies, by electroosmosis. Generally, the combined skin-contacting areas of electrode assemblies 18 and 19 can range from about 1 $cm^2$ to about 200 $cm^2$, but typically will range from about 5 $cm^2$ to about 50 $cm^2$.

The donor reservoir 24 and counter reservoir 25 of the electrotransport delivery device 10 must be placed in agent-transmitting or drug-transmitting relation with the patient, usually on the skin, to deliver the agent or drug by electrotransport. Usually, this requires either that the reservoirs 24 and 25 themselves be placed in intimate contact with the patient's skin; or, when using the optional ion-conducting in-line adhesive layers 27 and 28, these adhesive layers are placed in intimate contact with the patient's skin (i.e., after removal of the release liner 29). Various sites on the human body may be selected for placement of the device 10, depending upon the physician's or the patient's preference, the drug or agent delivery regimen, or other factors such as cosmetic.

Figure 2:
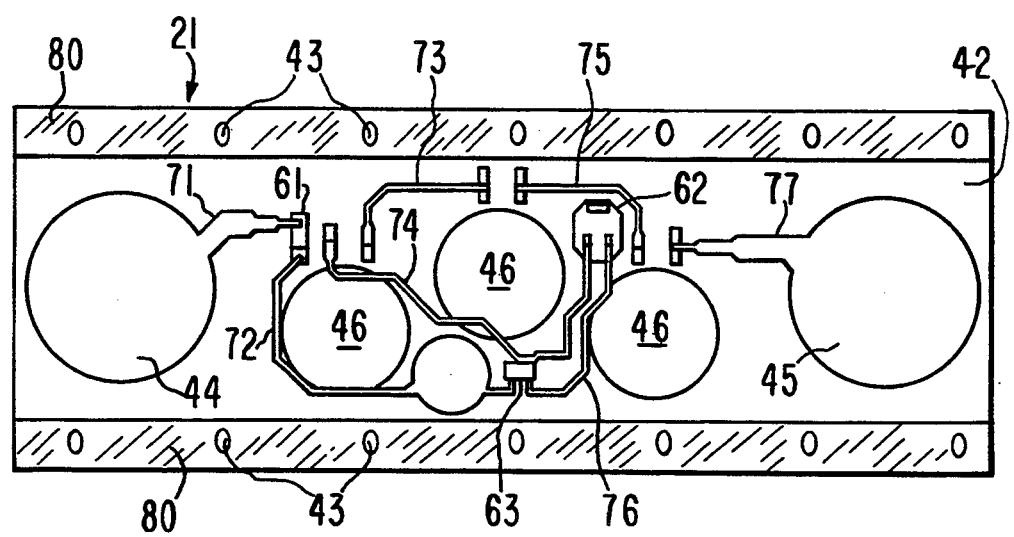
FIG. 2 is a schematic top view of an electrical circuit useful in the electrotransport delivery device of the invention.

FIG. 2 illustrates an electrical circuit which may be used in accordance with the present invention. The circuit 21 includes a non-conductive flexible substrate 42 and a plurality of electrical components and electrically conductive pathways, such as circuit traces, thereon. The substrate 42 is preferably a flexible polymer sheet such as a polyester or polyimide film.

A "keep-out" or exclusion zone 80 is optionally provided along the lengthwise edges of substrate 42, and is shown by cross-hatching in FIG. 2. The exclusion zone 80 provides a perimeter space in which, for example, sprocket holes 43 or other film transport means may be provided. The sprocket holes 43 provide a means for conveying substrate 42 from, for example, a continuous roll of substrate stock and allow a plurality of circuits 21 to be rapidly assembled in a continuous fashion. In this manner, low cost, relatively inexpensive flexible circuits can be produced. Typical dimensions for the substrate 42 would be a total film width of about 1–4 cm, a length of about 2–15 cm, a "keep-out" zone width of about 0.1–0.5 cm, and a film thickness of about 0.02–0.08 mm.

The circuit 21 includes circuit traces 71 and 77 that end in large, circularly shaped terminals 44 and 45, respectively. Terminal 44 is adapted to be electrically connected (either through direct contact or indirectly through a solderless electrical conductor such as an electrically conductive adhesive) to an electrode 22. Similarly, terminal 45 is adapted to be electrically connected to an electrode 23. As shown, terminal 44 is electronically connected through the remainder of circuit trace 71 to a resistor 61. Other circuit components that can be mounted on the substrate 42 include a variable resistor 62 and a field effect transistor 63. Three 3-volt button cell batteries (not shown) are adapted to be mounted in series on the substrate 42 within three circularly-shaped areas 46. Additional circuit traces 72, 73, 74, 75, 76 and 77 interconnect the batteries (not shown) and the electrical components 61–63.

Circuit traces 71–77 (including terminals 44 and 45) can be deposited on a polyester polyimide substram 42 by conventional techniques, such as silk screening or pad printing. Appropriate silk screening techniques are described in U.S. Pat. No. 5,050,498, issued to Smith, and U.S. Pat. No. 5,100,695, issued to Kawakami et al, which are incorporated herein by reference, and in *Screen Process Printing* by A. V. Schwalbach and J. A. Schwalbach, Van Nostrand Reinhold Company, 1970, pp. 99–105. Appropriate pad printing techniques are described in U.S. Pat. No. 4,745,857, issued to Putnam et al, U. S. Pat. No. 4,896,598, issued to Leech et al, No. 4,779,531, issued to Ueno et al, U. S. Pat. No. 4,928,587, issued to Glover and No. 5,066,360, issued to Daley et al, which are incorporated herein by reference.

An alternative to printing circuit traces on the substrate 42 by silk screening or pad printing uses a substrate 42 made by a known two-step injection molding process, followed by selectively plating the substrate 42. This alternative process is disclosed in U.S. Pat. Nos. 4,917,761, 4,978,569 and 4,985,293, all issued to Keep, which are incorporated herein by reference. According to this alternative process, a molded film substrate is deposited as a first injection molding shot of a non-plateable resin. Next, a plateable, non-conductive resin is deposited at predetermined locations on the film substram formed in the first injection molding shot. The plateable resin is then chemically treated to accept a conductive plating, for example, from an electrochemical bath. An electrically conductive plating is then applied. The bath selectively plates only those portions of the substram formed in the second injection molding shot, thereby defining the electrically conductive traces.

According to the present invention, the circuit traces deposited on the substrate 42 of FIG. 2 are composed of conductive materials that are relatively non-toxic. Whether a conductive material is considered toxic or poisonous depends, not only on the inherent potency and site specificity of a material, but also on how well the patient's body can dispose of the material. Thus, the toxicity of a material is dependent upon a complex set of biological phenomena, including the rate of absorption, the distribution within the body, the biotransformation and the excretion of the material. Ultimately, the concentration of a material at a specific site determines toxicity. The relative toxicity of a conductive material may be determined using a recognized toxicology handbook, such as: *Patty's Industrial Hygeine and Toxicology*, John Wiley & Sons, New York, N.Y., 1981; *Clinical Toxicology of Commercial Products*, Williams and Wilkins, Baltimore, Md., 1984; and *Casarett and Doull's Toxicology: The Basic Science of Poisons*, Pergamon Press, Elmsford, N.Y., 1991.

When conventional printing techniques are used, the appropriate circuit pattern is deposited (e.g., by silk screening or pad printing) onto the substrate 42, using a liquid ink or other coating containing an electrically conducting material that is relatively non-toxic if delivered into the body. While metals generally exhibit good electrical conductivity, care should be taken in selecting the electrically conducting material because many materials (e.g., metals) are either toxic themselves or can form toxic soluble salts under conditions normally encountered during operation of an electrotransport delivery device. Suitable non-toxic electrically conducting materials include silver, carbon, graphite, gold, zinc, titanium and mixtures thereof. Of these materials, silver, carbon and graphite are preferred.

In addition to these non-toxic, electrically conductive materials, other noble metals, such as platinum, palladium and iridium may also be used. Platinum, palladium and iridium are relatively non-toxic in their respective metallic states but also have the ability to form salts (e.g., oxides and chlorides), which are either toxic or may cause irritation and/or sensitization reactions in the skin. However, because of the relative inertness of these noble metals, there is very little likelihood of forming a toxic noble metal salt under conditions normally encountered during operation of an electrotransport delivery device. Thus, the noble metals platinum, palladium and iridium are also considered to be non-toxic, electrically conductive materials, for purposes of this invention.

The ink or coating is also preferably substantially free of conductive materials that are potentially more toxic to the patient, such as lead, nickel, cadmium, and copper. More preferably, the ink is also substantially free of the following potentially toxic materials: tungsten, chromium and iron. The term "substantially free" of a given element or compound, as used herein, means having a concentration of less than 10 percent by weight of the given element or compound, more preferably less than 1 percent by weight, and most preferably less than 0.1 percent by weight.

The desired circuit pattern is deposited as traces on the substrate 42. The ink trace width is not critical, but is generally in the range 0.1–1 mm. In conventional silk screening, the wet ink pattern is deposited onto the substrate 42, and then dried at a temperature of $T=25°–250°$ C. in an inert atmosphere such as nitrogen.

The concentration of the electrically conducting material in the liquid ink can be varied to provide the desired electrical resistance for the trace width and trace length chosen for the ink, and to provide optimum adherence to the substrate film and to the electrically conductive adhesive used to electrically connect the various circuit components to the circuit traces. The composition and dimensions of the ink traces should allow current of at least 2 milliamps in the portion of the circuit defined by these traces, with no Ohmic heating problems or maximum voltage problems observed. Suitable conductive inks include the following ink products sold by Acheson (Port Huron, Mich.): (1) 423SS, including finely divided graphite particles suspended in a vinyl resin or other matrix, with electrical resistivity $\rho \approx 0.4$ Ohm-cm; and (2) 415SS, including finely divided silver particles suspended in a vinyl resin, with electrical resistivity $\rho \approx 0.001$ Ohm-cm.

Once the circuit traces are deposited on the substrate 42, components such as batteries, resistors, capacitors or transistors are attached to the substrate 42, using a nonconductive adhesive that holds the component in the proper position and orientation at the desired site. Once the electrical components are fixed on the substrate 42, the electrical leads (or terminals, where a battery is used) of each of these components must be electrically connected to the selected circuit traces.

In accordance with the present invention, electrical coupling of an electrical component to a circuit trace is accomplished using an electrically conductive coupling means that is substantially free of materials that are potentially toxic to the patient. Most preferably, the electrically conductive coupling means includes an adhesive, such as an epoxy adhesive, containing an electrically conducting material that is non-toxic if delivered into the body. Preferably, the electrically conducting material is selected from silver, carbon, graphite, gold, platinum, palladium, iridium, zinc, titanium and mixtures thereof. The adhesive is also preferably substantially free of electrically conductive materials that are potentially toxic to the patient, such as lead, nickel, cadmium and copper. More preferably, the adhesive is also substantially free of tungsten, chromium and iron. Silicone adhesives and acrylate adhesives, also containing a non-toxic electrically conducting material, may also be used in place of an epoxy adhesive. McGhan NuSil silicone R-2632 and R-2633, available from McGhan NuSil Corporation, Carpinteria, Calif. and having electrical resistivities of 0.04 and 0.004 Ohm-cm, respectively, are also suitable for this purpose.

In certain cases, it may be desirable to use the electrically conductive adhesive to structurally attach the electrical components to the substrate 42 as well as to couple the electrical leads or terminals of the components to the circuit traces. This approach may save one or more process steps.

Using this approach, attachment of an electrical component to a circuit trace does not use soldering so that lead or copper ions from soldered electrical connections or from solder-coated copper circuit traces are not present. No chemical cleaning of the circuit, with or without circuit attachments present, is required because neither soldering nor etching is performed during circuit fabrication. The preferred electrically conductive materials (e.g., silver, graphite, gold, platinum, palladium, iridium, zinc and titanium) contained in the ink and in the electrically conductive adhesive resists corrosion so that corrosion of the adhesive coupling means and circuit traces is not a problem. In the case of silver-containing inks and adhesives, even if silver contained in the ink or adhesive does come into contact with the electrolyte solution during operation and silver ions are generated and delivered into the body, elemental silver is relatively non-toxic compared with other metals, such as lead and copper.

Figure 6:
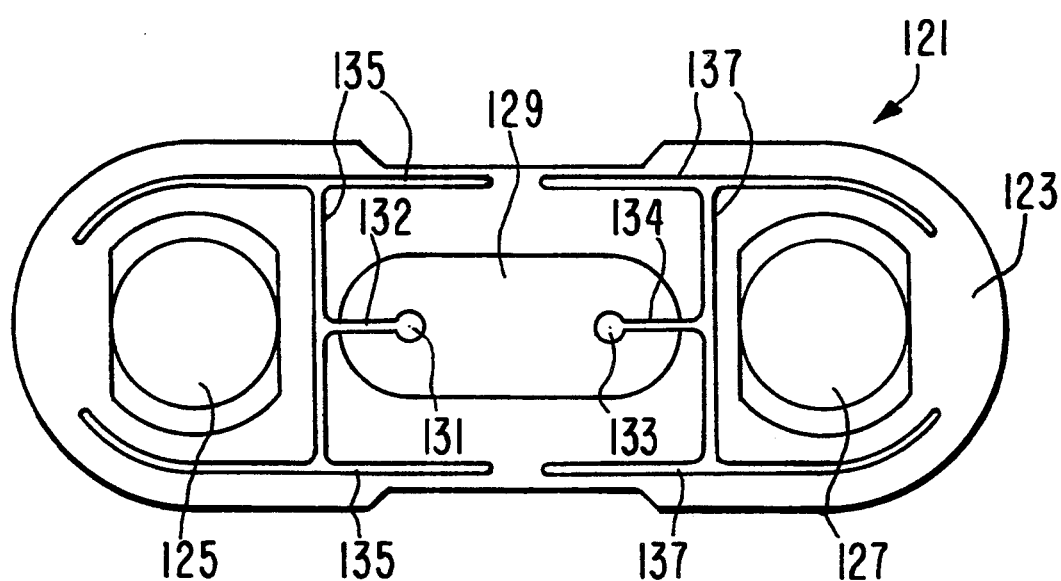
FIG. 6 is a schematic top view of a flexible substrate, with an electrical circuit printed thereon, that can be used in the invention.

The substrate 42 may be positioned between the layer of circuit components shown in FIG. 2 and one or more of the electrodes 22 and 23. Alternatively, the substrate 42 may be positioned "above" the remainder of the apparatus shown in FIGS. 1 and 2 so that the layer of circuit components lies between the substrate 42 and one or more of the electrodes 22 and 23. In this "upside down" circuit configuration, a separate substrate 42 and backing layer 17 may be unnecessary. For example, FIG. 6 illustrates another embodiment 121 of the invention in which the electrically conductive circuit traces 135 and 137 are printed or deposited directly on the underside of a molded rubber backing piece 123. The backing piece 123 performs a function similar to that of the backing layer 17 illustrated in FIG. 1 and acts as a flexible substrate for receiving the printed or deposited circuit traces 135 and 137.

The backing piece 123 may be formed of rubber or other moldable polymer. Two optional, spaced apart depressions 125 and 127 are molded into the backing piece 123. The depressions 125 and 127 are optionally provided to accept pouches (not shown) containing water or another liquid solvent that enables the liquid to be released from the pouches into the dry reservoirs 24 and 25 (FIG. 1) to hydrate these reservoirs just before use of the device. A third depression 129 serves as a space for holding one or more batteries or, optionally, other electrical components for controlling the amplitude, polarity, timing, waveform shape, etc. of the electric current supplied by the batteries. In the relatively simple circuit illustrated in FIG. 6, two button cell batteries, connected in series or parallel, may be placed in side-by-side relation (not shown) within the depression 129. In a series configuration, the positive terminal of one battery is electrically connected, using conductive adhesive, to the terminal 131, and the negative terminal of the other battery is electrically connected, using conductive adhesive, to the terminal 133. The battery output terminals 131 and 133 are electrically connected to the circuit traces 135 and 137 by circuit traces 132 and 134, respectively. The circuit traces 135 and 137 each have a configuration resembling a distorted "I" and are adapted to be electrically connected to the donor and counter electrode assemblies (not shown in FIG. 6).

Figure 3:
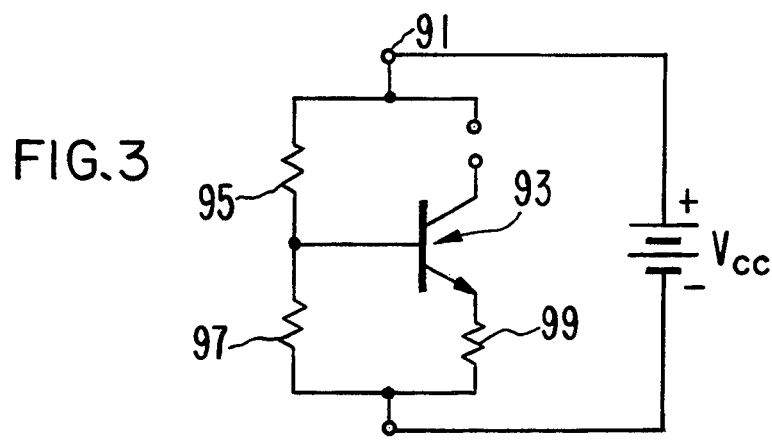
FIGS. 3-5 are schematic illustrations of electrical circuits that can be used in the electrotransport delivery device of the present invention.
Figure 4:
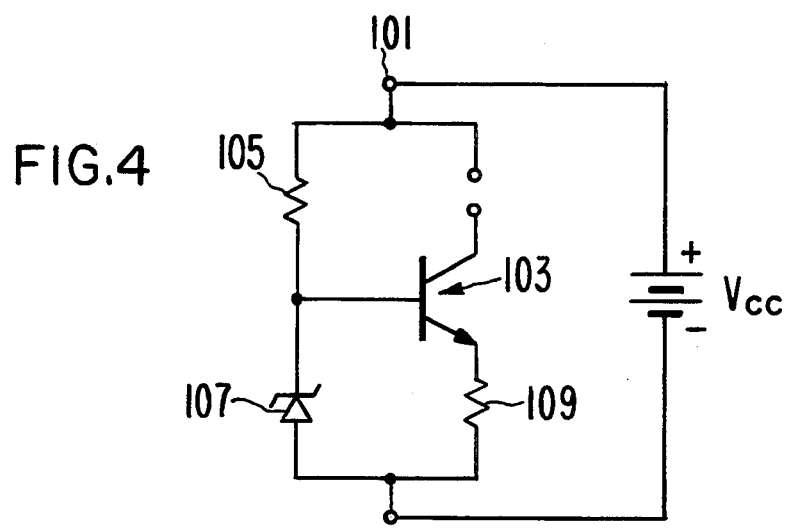
Figure 5:
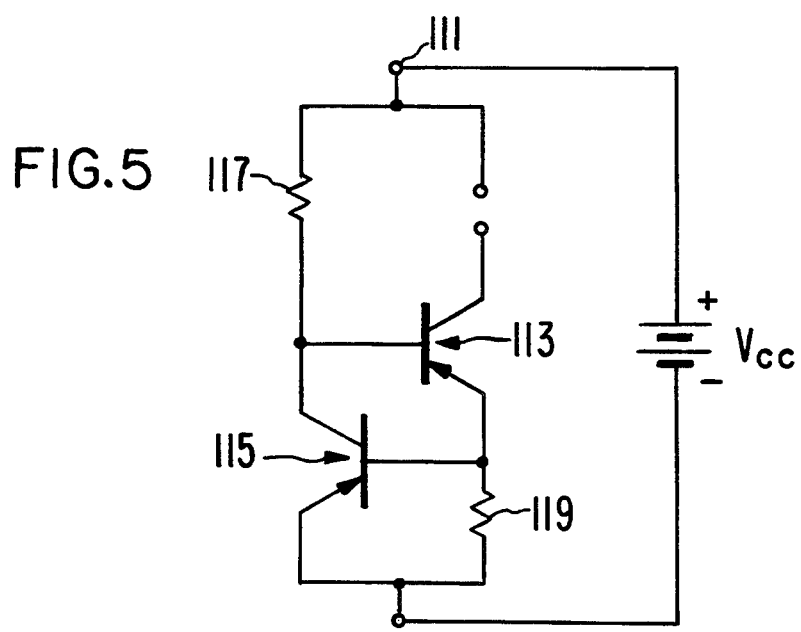

FIGS. 3, 4 and 5 illustrate examples of known electrical circuits suitable for use in an electrotransport delivery device in accordance with the present invention. FIG. 3 uses a voltage source 91 ($V_{cc}$=1–5 Volts), a (bipolar) transistor 93 with current gain$\approx$3–30, two resistors 95 and 97 connected in series between $V_{cc}$ and ground, and connected at a common end to the transistor base terminal, and a third resistor 99 connected between the transistor emitter terminal and ground. The voltage difference provided across the load 100 (e.g., a portion of a human body) is approximately equal to $V_{cc}R_{95}/(R_{95}+R_{97})$, where $R_{95}$ and $R_{97}$ are the resistance values of the respective resistors 95 and 97.

FIG. 4 uses a voltage source 101, a transistor 103, a resistor 105 and a Zener diode 107 connected in series between $V_{cc}$ and ground and connected at a common end to the transistor base terminal, a resistor 109 connected between the emitter terminal and ground. Voltage difference across the load is approximately $V_{cc}-V_Z$, where $V_Z$ is the cathode-anode voltage difference ($\approx$constant) for the Zener diode 107.

FIG. 5 uses a voltage source 111, two transistors 113 and 115 with the base terminal of 113 connected to the collector terminal of 115, and with the base terminal of 115 connected to the emitter terminal of 113, a resistor 119 connected between the emitter terminal of the transistor 113 and ground, and a resistor 117 connected between the base terminal of transistor 113 and $V_{cc}$. The voltage difference across the load is approximately $V_{cc}-\Delta V_{be}-0.6$ Volts, where $\Delta V_{be}$ is the base-emitter voltage difference for the transistor 113.

Circuits that can be fabricated according to the invention are not limited to those illustrated in FIGS. 3–6. Any circuit with components such as batteries, transistors and passive impedance control components (inductors, resistors, capacitors, etc.) may be fabricated using the invention. The invention allows circuit trace definition and circuit component mounting on the circuit at selected positions, using the same (automatable) procedures for all circuit components, including batteries.

I claim:

1. An electrotransport device for delivery of a beneficial agent through a body surface of a patient, the device comprising:

first and second electrode assemblies, at least one of the electrode assemblies containing the beneficial agent to be delivered;

electrical circuit means for electrically connecting the first electrode assembly to the second electrode assembly through the electrical circuit means, the electrical circuit means including at least one electrically conductive circuit trace positioned on a substrate and including at least one electrical component which is electrically connected to the circuit trace by an electrical connection means wherein the circuit trace is comprised of an electrically conductive ink or coating and the circuit trace and the electrical connection means each have a resistivity of less than about 0.01 ohm-cm and each are substantially free of electrically conductive materials which are toxic to the patient.

2. The device of claim 1, wherein said conductive ink or coating contains an electrically conductive material selected from the group consisting of silver, gold, platinum, palladium, iridium, zinc, titanium, and mixtures thereof.

3. The device of claim 2, wherein said electrically conductive material is present in the form of particles or flakes.

4. The device of claim 1, wherein said conductive ink or coating is substantially free of lead and copper.

5. The device of claim 4, wherein said conductive ink or coating is substantially free of nickel, cadmium, chromium, tungsten and iron.

6. The device of claim 1, wherein said electrical connection means comprises an electrically conductive adhesive.

7. The device of claim 6, wherein said adhesive comprises a material selected from the group consisting of epoxy adhesive, silicone adhesive and acrylate adhesive.

8. The device of claim 6, wherein said adhesive contains an electrically conductive material selected from the group consisting of silver, gold, platinum, palladium, iridium, zinc, titanium, and mixtures thereof.

9. The device of claim 6, wherein said adhesive is substantially free of lead and copper.

10. The device of claim 9, wherein said adhesive is substantially free of nickel, cadmium, chromium, tungsten and iron.

11. The device of claim 1, wherein said electrical component is attached to said substrate using a non-conductive adhesive.

12. The device of claim 1, wherein said electrical component comprises a resistor or variable resistor.

13. The device of claim 1, wherein said electrical component comprises a transistor.

14. The device of claim 1, wherein said electrical component comprises a battery.

15. The device of claim 1, wherein said substrate is positioned between at least one of said electrode assemblies and said conductive trace.

16. The device of claim 1, wherein said circuit trace is positioned between said substrate and at least one of said first and second electrode assemblies.

17. The device of claim 16, wherein said substrate is formed of a molded rubber or other moldable polymer.

18. The device of claim 16, wherein said substrate comprises a water-impermeable backing for the device.

* * * * *